United States Patent [19]
Goble et al.

[11] Patent Number: 5,584,860
[45] Date of Patent: Dec. 17, 1996

[54] SUTURE ANCHOR LOADER AND DRIVER

[75] Inventors: E. Marlowe Goble; Alan Chervitz; David P. Luman, all of Logan, Utah; George A. Perakis, Haverhill, Mass.

[73] Assignee: Mitek Surgical Products, Inc., Westwood, Mass.

[21] Appl. No.: 389,149

[22] Filed: Feb. 15, 1995

[51] Int. Cl.$^6$ .................................................. A61B 17/00
[52] U.S. Cl. ........................ 606/232; 606/75; 606/104; 623/13
[58] Field of Search ............................ 606/232, 104, 606/75, 73, 72, 60, 53, 99, 86, 139, 148; 623/13

[56] References Cited

U.S. PATENT DOCUMENTS

| | | | |
|---|---|---|---|
| 5,207,679 | 5/1993 | Li | 606/232 |
| 5,224,946 | 7/1993 | Hayhurst et al. | 606/72 |
| 5,258,016 | 11/1993 | DiPoto et al. | 606/232 |
| 5,354,298 | 10/1994 | Lee et al. | 606/144 |
| 5,411,506 | 5/1995 | Goble et al. | 606/104 |
| 5,443,482 | 8/1995 | Stone et al. | 606/232 |

Primary Examiner—Michael Powell Buiz
Assistant Examiner—Jeffrey A. Schmidt
Attorney, Agent, or Firm—Pandiscio & Pandiscio

[57] ABSTRACT

A suture anchor loader and driver for mounting a suture anchor with a connected suture, that is arranged for mounting and maintaining the suture to the driver distal end while driving the anchor into a bone, whereafter the driver is removed from the anchor, leaving the suture extending from the seated anchor. The driver includes a cylindrical solid body and has an anchor mount formed as its distal end that is for receiving a coupling end of the anchor fitted therethrough and includes a center longitudinal passage, wherethrough the anchor suture is fitted. A first curved passage is formed in the driver body distal end and intersects the center longitudinal passage through the anchor mount, and extends to the driver body surface where it intersects a straight longitudinal groove that is formed along the driver body. The groove intersects, on its proximal end, an inlet end of a second curved passage that extends through and exits the driver body surface on the opposite side to the longitudinal groove and first curved passage end, which first curved passage, longitudinal groove and second curved passage are to receive the suture threaded therethrough. The invention provides several embodiments of arrangements for maintaining the threaded suture alongside the driver body, and provides, on the driver body proximal end, a drill coupling arrangement that is to fit into and be turned by a conventional drill, T-handle, or the like, for seating the anchor into a bone material.

16 Claims, 11 Drawing Sheets

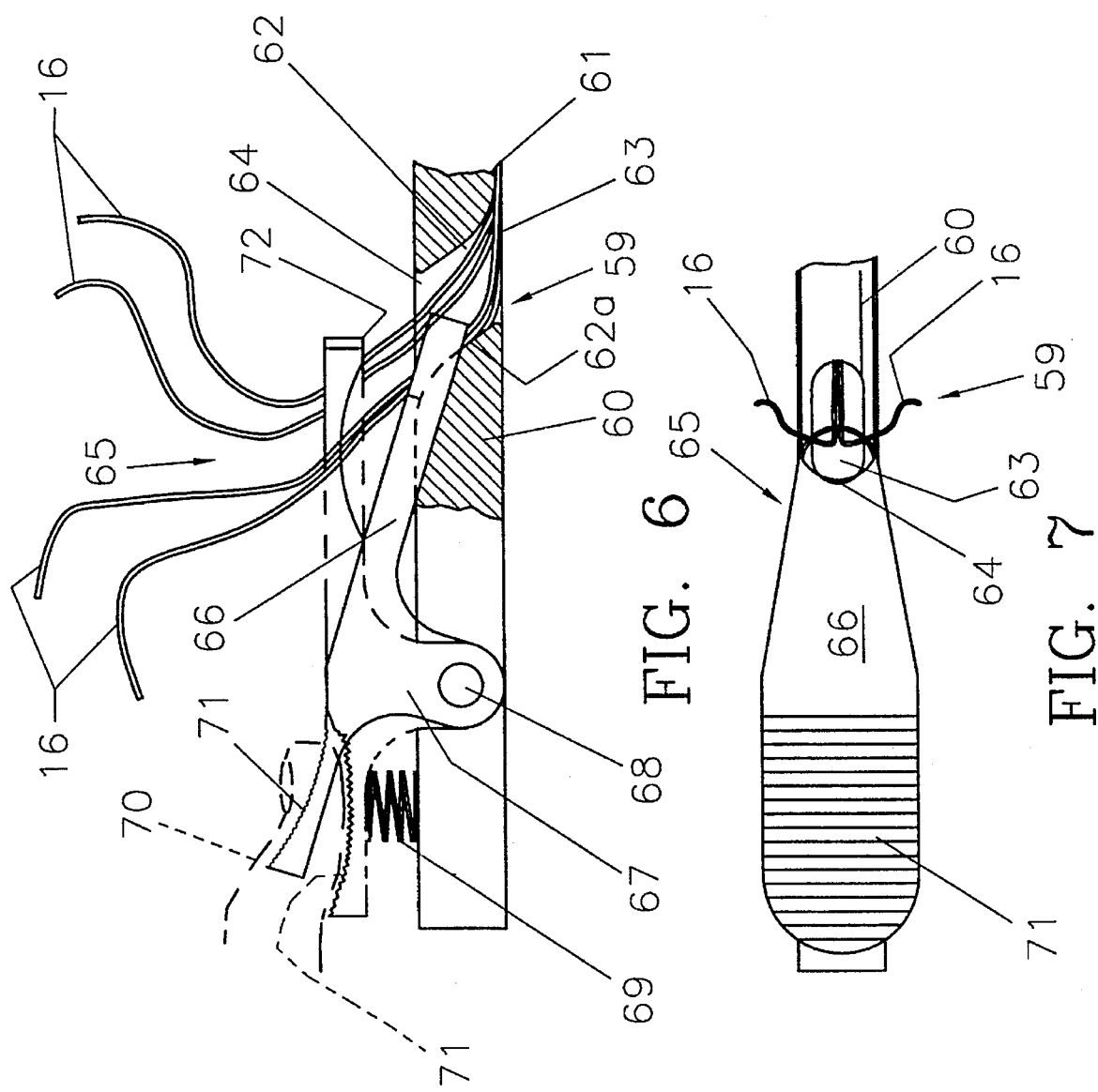

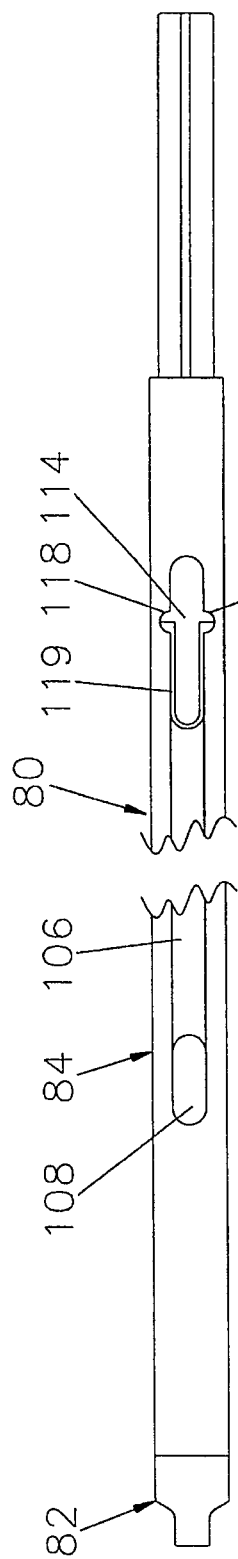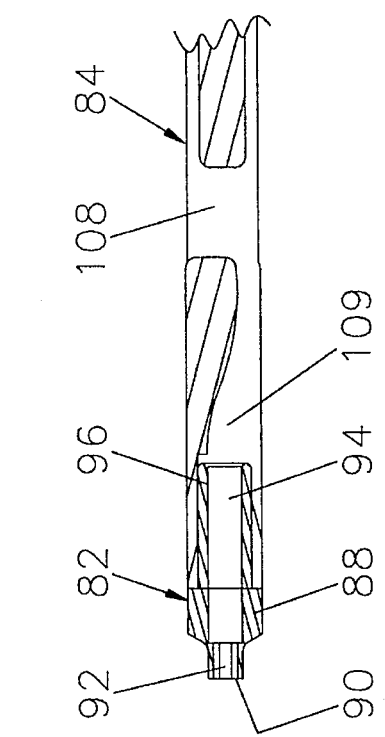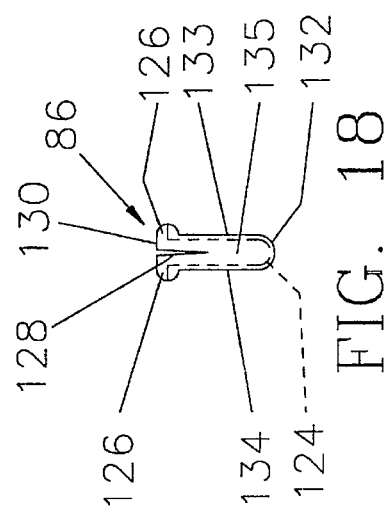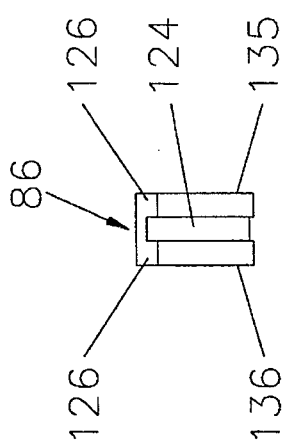

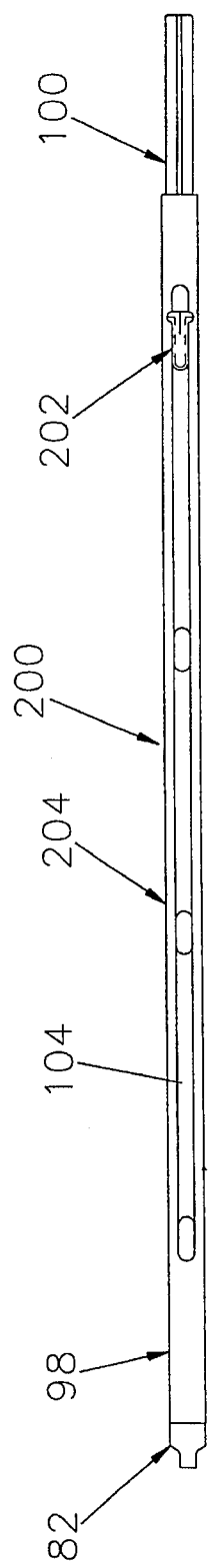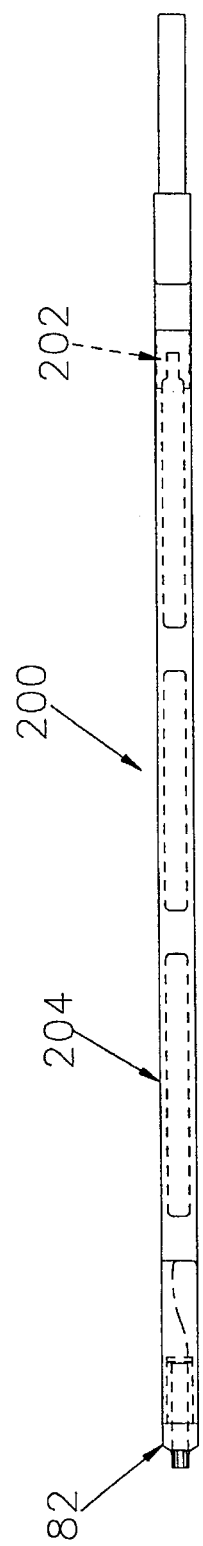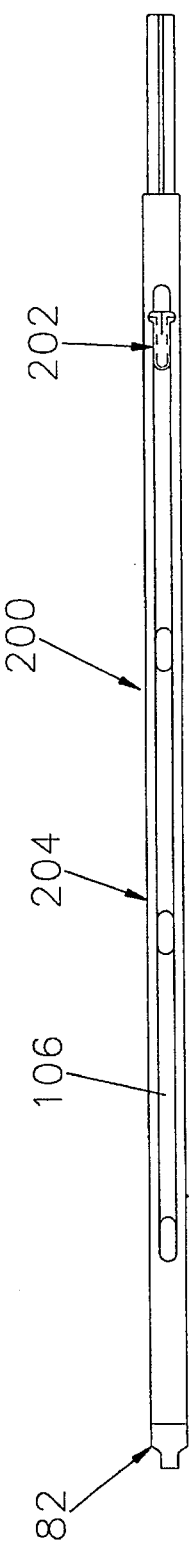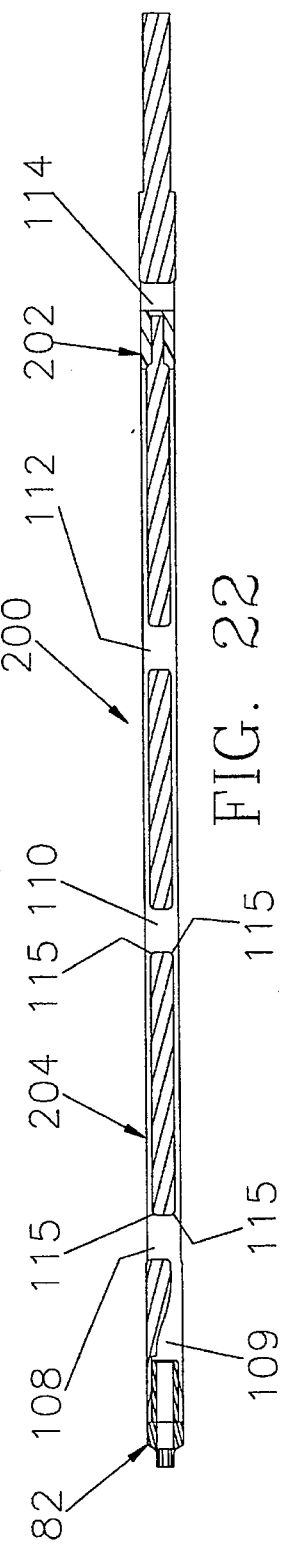

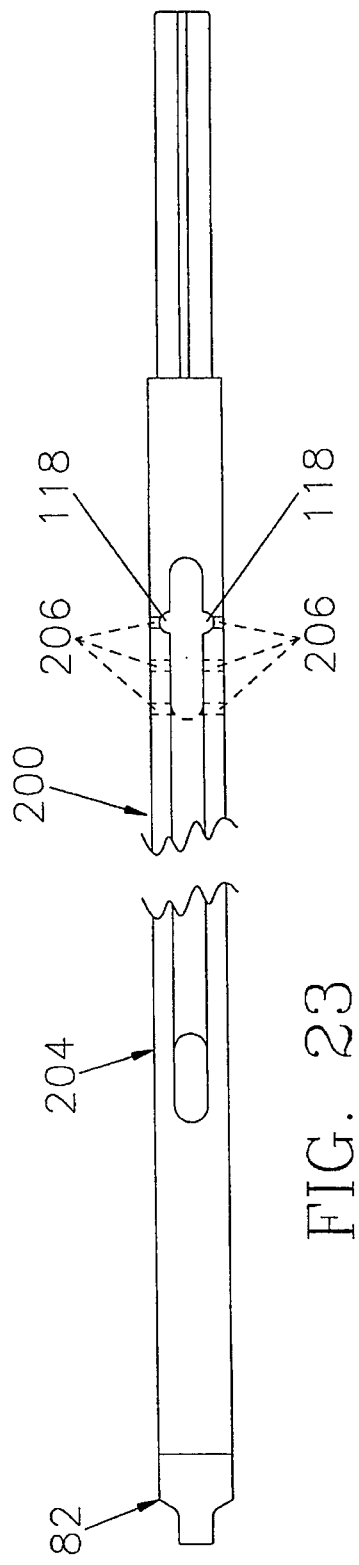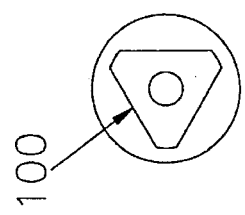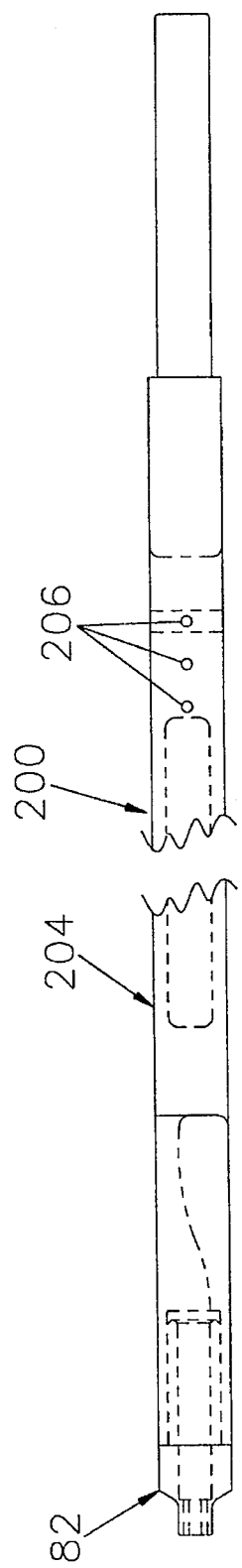

5,584,860

SUTURE ANCHOR LOADER AND DRIVER

BACKGROUND OF THE INVENTION

1. Field of the Invention

This invention relates to medical equipment and in particular to drivers for mounting an anchor device that include a suture that is secured to the anchor and is maintained in the driver, the driver for use in deploying the anchor device into a bone for maintaining a section of soft tissue thereto.

2. Prior Art

Driver devices for use for both positioning an anchor or fastener or the like that includes a suture secured thereto onto a bone surface location whereat a section of soft tissue, or the like, is to be attached are well known. A number of earlier inventions of one of the present inventors show anchor drivers. For example, such a driver is shown in a U.S. Patent to E. Marlowe Goble, U.S. Pat. No. 4,632,100, that involves a driver arranged for mounting an anchor on a forward end thereof, with a suture connected to the anchor rear end that is contained in a driver center longitudinal cavity. Additionally, several of the applicants have filed U.S. patent applications for an Anchor Driver, Ser. No. 08/225,768, now U.S. Pat. No. 5,411,506 and a Suture Anchor and Driver Combination, Ser. No. 08/225,791, now U.S. Pat. No. 5,411,523 that involve anchor and driver combinations and provide for maintaining a suture within the driver body. Unlike these devices, however, the present invention is in a driver that is arranged to receive and mount an anchor to a distal end thereof and provides for conveniently threading a suture extending from which anchor rear end through and along the driver body, and for maintaining that suture to the driver body while the driver is driven to deploy the anchor into a bone or bone-like material. Whereafter, the driver of the invention is easily separated from the anchor, with the suture connected to the anchor rear end easily released therefrom.

A use of the anchor and driver of the above cited U.S. Pat. No. 4,632,100 is shown in another patent to one of the inventors, U.S. Pat. No. 5,037,426. Additionally, other patents to one of the present inventors, U.S. Pat. Nos. 4,738,255 and 5,013,316, illustrate other driver and anchor combinations. Further, a number of combinations of anchors and drivers some of which include arrangements for capturing, maintaining and fitting sutures extending from seated anchors are shown in U.S. Pat Nos. 4,779,616; 4,946,468; 5,071,420; 5,100,417; 5,102,421; 5,139,520; 5,207,679; 5,211,650; 5,224,946; 5,236,445; and 5,258,016. None of which patents as cited above, however, involve a loader and driver combination that is like that of the invention that provides for rapidly and conveniently fitting an anchor mounted suture therethrough and for maintaining that suture to the driver body as the driver is driven so as to deploy the anchor into a bone.

SUMMARY OF THE INVENTION

It is therefore, a principal object of the present invention to provide a suture anchor loader and driver arranged for mounting an anchor on a forward or distal end thereof that provides for conveniently threading a suture, that is connected to the anchor end, therethrough and for maintaining that suture to the driver body as the driver is driven to deploy the anchor into a bone or bone like material.

Another object of the present invention is to provide a suture anchor loader and driver that includes a cylindrical body having a plurality of intersecting passages and a groove disposed serially therealong that are to receive and maintain a suture threaded therethrough from an anchor end which anchor is releasably mounted onto the driver body distal end.

Another object of the present invention is to provide a suture anchor loader and driver arranged to mount an anchor device to a forward or distal end whereto a suture is connected, the suture to be conveniently threaded through the driver and maintained onto the driver body as the driver is driven to deploy the anchor device into a bone, or bone like material.

Still another object of the present invention is to provide a suture anchor loader and driver that has a body arranged to be conveniently fitted with a suture extending from a suture anchor device mounted onto a driver distal end, and provides for releasably maintaining the suture to the driver body as the driver is driven so as to deploy the anchor device into a bone or bone like material, whereafter the suture is easily separated from the driver body.

Still another object of the present invention is to provide a cylindrical driver arranged to be conveniently fitted with an anchor device mounting a suture with the anchor device for use in a surgical procedure, the driver for driving to deploy the anchor device into a bone or like material, and is then easily separated from the anchor device and suture.

Still another object of the present invention is to provide an improved method for attaching suture to bone.

In accordance with the above objects, the present invention is in a suture anchor loader and driver that is arranged for mounting an anchor device on a driver distal end, the anchor device for mounting in a bone, or like material, with a suture extending from the anchor device. The driver includes a cylindrical body with spaced lateral holes and a groove formed therein that the suture is threaded through and provides for maintaining the suture onto the driver body during deployment of the anchor.

The driver includes a body that is preferably a straight cylindrical section formed from a biocompatible material that is suitable for use in a surgical procedure. The cylindrical body includes an anchor mount that is formed as a driver forward or distal end. The anchor mount is preferably a cylindrical collar formed to have a sided inner circumference to accommodate a like sided outer surface of an anchor rear coupling end, and includes a center narrow opening formed axially through the collar center. Preferably, the anchor rear coupling end is formed to have a hexagon cross section as its connection surface, that is for fitting into the collar, engaging the collar inner side walls that have a like hexagon cross section.

The driver cylindrical body includes a center longitudinal passage or first hole formed through the collar in its distal end that curves to exit the body side adjacent to a longitudinal groove that has been formed along the driver body. The groove extends across a driver body mid-section and has, as its proximal end, an entrance to a second hole formed across and through the driver body. A suture retainer is fitted to the body adjacent to an exit opening of the second hole that is for retaining a suture fitted therethrough. The driver body, on its proximal end, is formed with a coupling section that is preferably sided for fitting into a turning device, such as a chuck of a standard drill, for turning the driver.

In practice, an end of a suture or suture strands are connected to, so as to extend from, the anchor rear end whereto the driver distal end is connected. The suture strand or strands are passed through the narrow opening in the driver collar, to exit the first passage, travel along the longitudinal groove and are threaded through the second passage. The suture strand or strands are pulled through the second hole, drawing the anchor rear coupling end into the driver cylindrical collar, and are fitted through so as to be maintained by the suture retainer alongside the driver body. The anchor device is thereby maintained onto the driver distal end for turning into a bone or bone-like material by rotating of the driver at its proximal end.

BRIEF DESCRIPTION OF THE DRAWINGS

These and other objects and features of the invention will become more fully apparent from the following description, in which the invention is described in detail in conjunction with the accompanying drawings. In which drawings:

FIG. 6 is an enlarged side elevation view of an end portion of the driver body that is adjacent to the exit end of a second hole formed therethrough and showing a second embodiment of a suture retainer as an alligator clamp mounted thereto;

FIG. 7 is a view like that of FIG. 6 but rotated ninety (90) degrees to show a top plan view of the second embodiment of the suture retainer;

FIG. 15 is an enlarged side elevational view of the anchor driver shown in FIG. 10, with the driver's suture retaining plug having been removed from the drawing;

FIG. 16 is an enlarged cross-sectional view of the driver shown in FIG. 11, with the driver's suture retaining plug having been removed from the drawing;

FIG. 17 is an enlarged side elevational view of the suture retaining plug;

FIG. 18 is an enlarged side elevational view of the suture retaining plug, with the suture retaining plug having been rotated 90 degrees from the position shown in FIG. 17;

FIG. 19 is a side elevational view of still another embodiment of an anchor driver formed in accordance with the present invention;

FIG. 20 is a side elevational view of the anchor driver shown in FIG. 19, rotated 90 degrees about its longitudinal axis, and showing the internal structure of the device in phantom;

FIG. 21 is a side elevational view of the anchor driver shown in FIG. 19, rotated 180 degrees about its longitudinal axis;

FIG. 22 is a cross-sectional view of the anchor driver shown in FIG. 19, rotated 270 degrees about its longitudinal axis;

FIG. 23 is an enlarged side elevational view of the anchor driver shown in FIG. 19, with the driver's suture retaining plug having been removed from the drawing;

FIG. 24 is an end view of the driver shown in FIG. 23;

FIG. 25 is an enlarged side elevational view of the anchor driver shown in FIG. 20, with the driver's suture retaining plug having been removed from the drawing;

DETAILED DESCRIPTION

Figure 1:
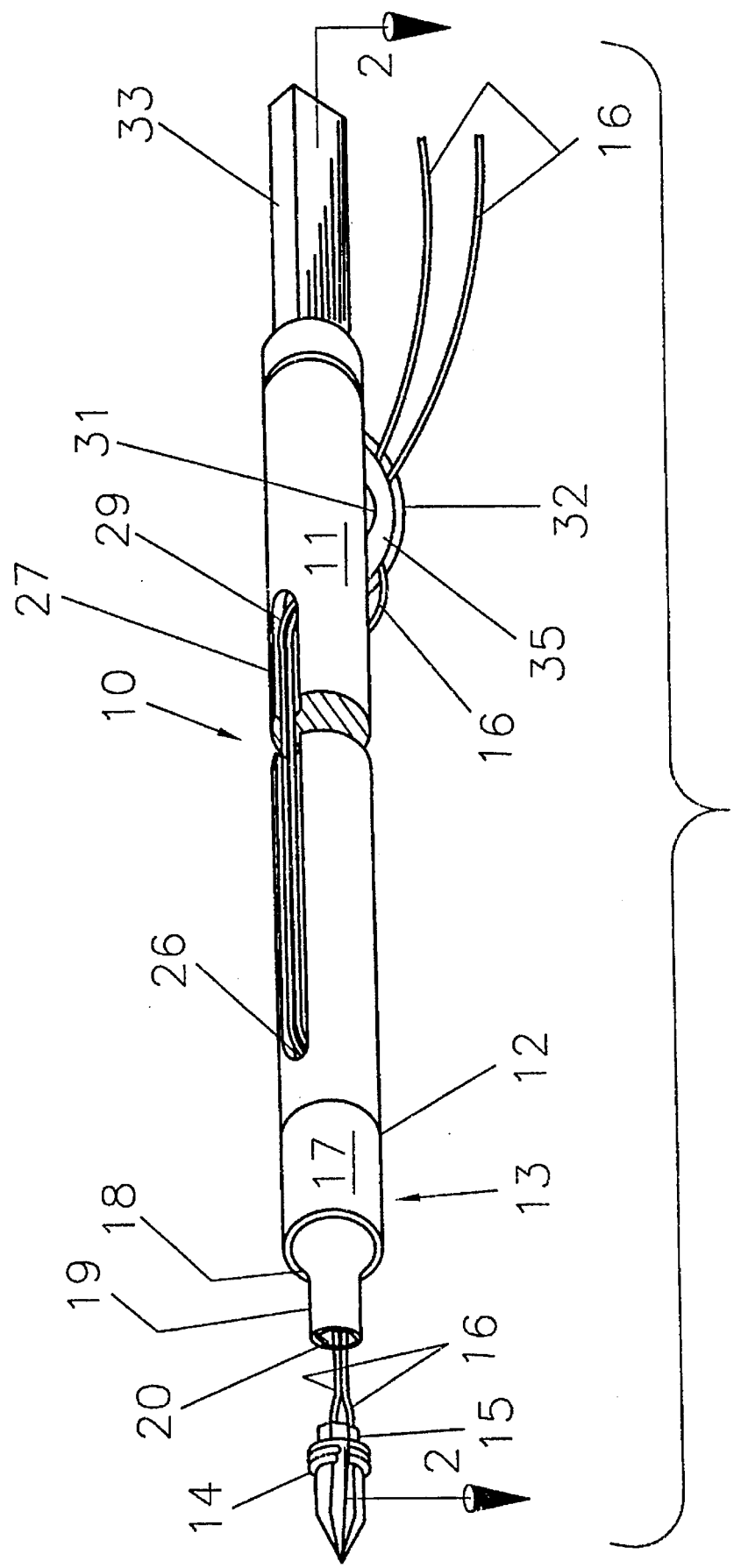
FIG. 1 is a side elevation distal end perspective view of a suture anchor loader and driver of the invention showing an anchor device, including a suture extending from a rear or coupling end thereof, exploded off of the driver distal end, and showing a section of a body of the driver removed illustrating that the driver may be formed from a biocompatible metal, and showing a suture extending from the anchor device threaded through openings and along a longitudinal groove formed in the driver body, and maintained to the driver body and showing a driver proximal end formed to be received by a drill chuck for turning.

FIGS. 1 through 5 show a first embodiment of a suture anchor loader and driver 10, hereinafter referred to as driver 10.

The driver 10, shown in FIGS. 1 through 5, includes a straight cylindrical body 11 that is preferably formed from a biocompatible material such as surgical grade stainless steel, various of the surgical grade polymers, etc., of the sort suitable for use in a surgical procedure on a human, and includes a forward or distal end 12 that is capped by an anchor mount 13. The anchor mount 13 is also preferably formed from a solid biocompatible material, e.g. stainless steel, as shown best in FIGS. 2 and 3, suitable for use in a surgical procedure practice on a human. Anchor mount 13 is to receive a coupling end 15 of an anchor 14 whereto is connected a suture 16, shown as consisting of two suture strands. The anchor 14 is preferred for use with all the embodiments of the invention, as shown best in FIG. 1, and, it should be understood, is preferably an anchor that is like that shown and described in earlier patents and patent applications of one or more of the inventors. For example, U.S. Pat. No. 4,632,100 shows an example of an anchor that is like anchor 14, as does a U.S. patent application, Ser. No. 08/225,768 of several of the present inventors, that shows a like anchor. Accordingly, the anchor 14 and mounting of suture 16 will not be further described, it being understood that the anchor 14 and its functioning is fully described in the above cited U.S. patent and patent application.

The driver anchor mount 13, as shown in FIGS. 1 through 5, has a cylindrical mid section 17 that necks inwardly at 18 into a forward or distal end 19 wherein is formed a center longitudinal anchor coupling hole 20. The coupling hole 20 is to receive, as shown in FIG. 1, the coupling end 15 of the anchor 14 fitted therein. To provide a secure mounting of the anchor coupling end 15 in coupling hole 20 the coupling end 15 is formed to have flat sides that are joined at their edges so as to form a sided cross section around its outer surface with a like configuration formed around the coupling hole 20 inner circumference. Which sided end and coupling hole walls, as shown in FIG. 1, preferably have a hexagon cross section for maintaining the anchor 14 in the driver 10 coupling hole 20.

Figure 2:
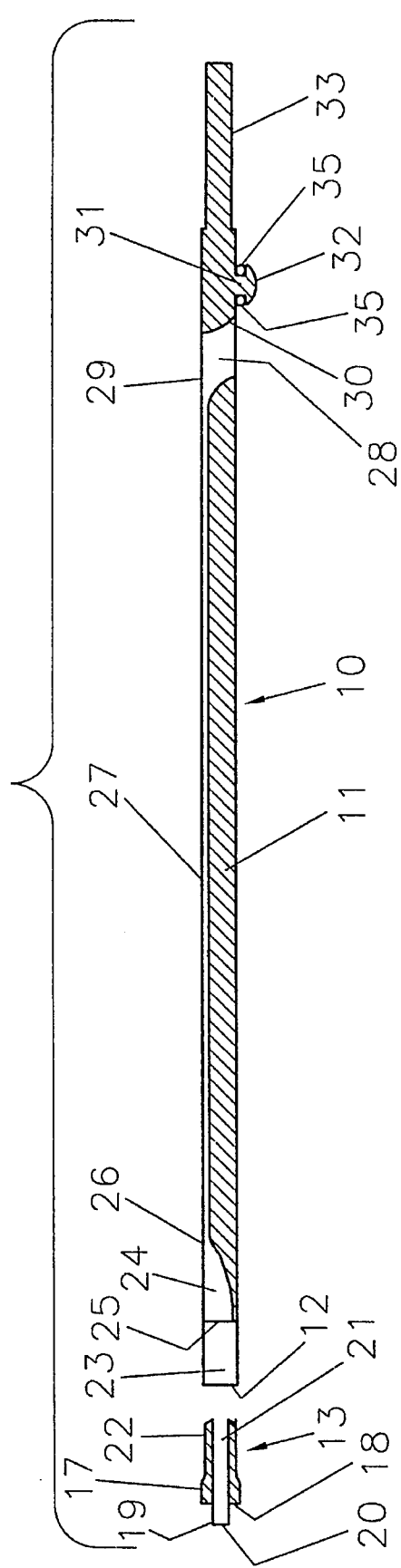
FIG. 2 is a reduced side elevation sectional view taken along the line 2—2 of FIG. 1.
Figure 3:
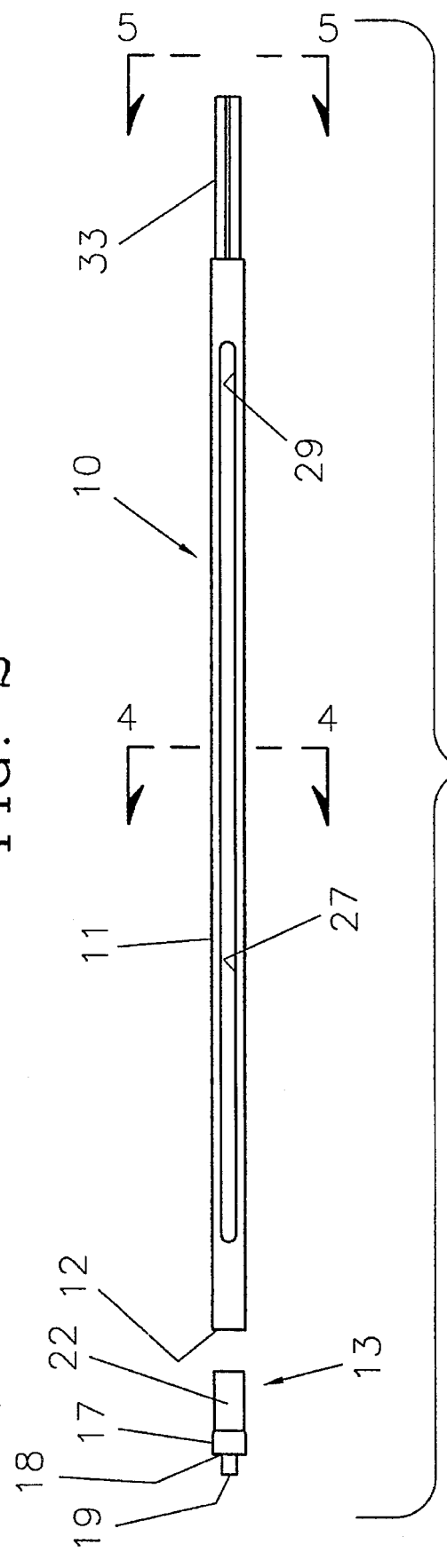
FIG. 3 is a view of the driver of FIG. 2 shown turned ninety (90) degrees.
Figure 5:
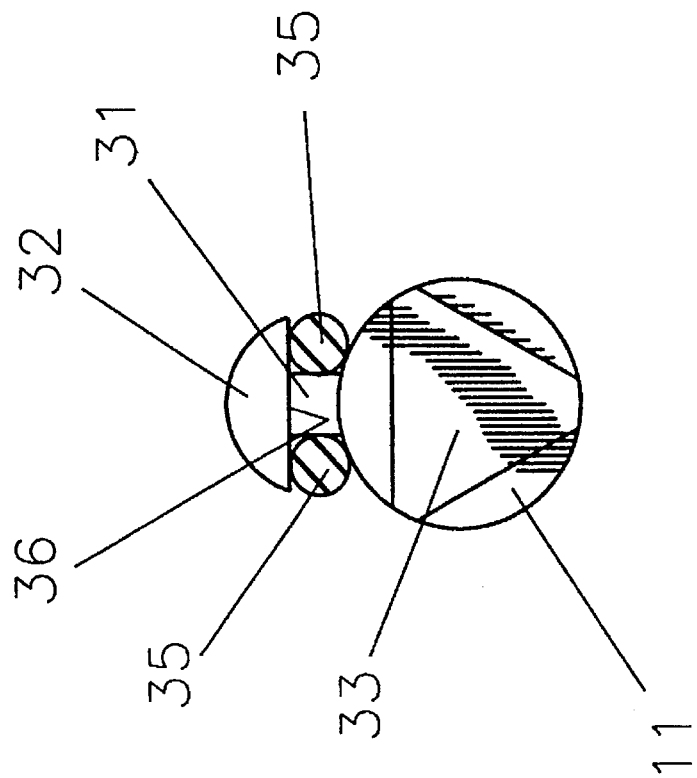
FIG. 5 is an enlarged cross sectional view taken along the line 5—5 in FIG. 3.
Figure 4:
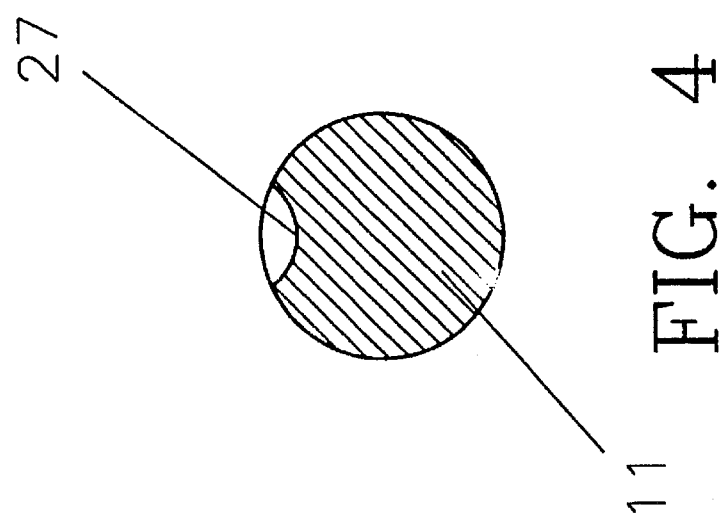
FIG. 4 is an enlarged cross sectional view taken along the line 4—4 in FIG. 3.
Figure 8:
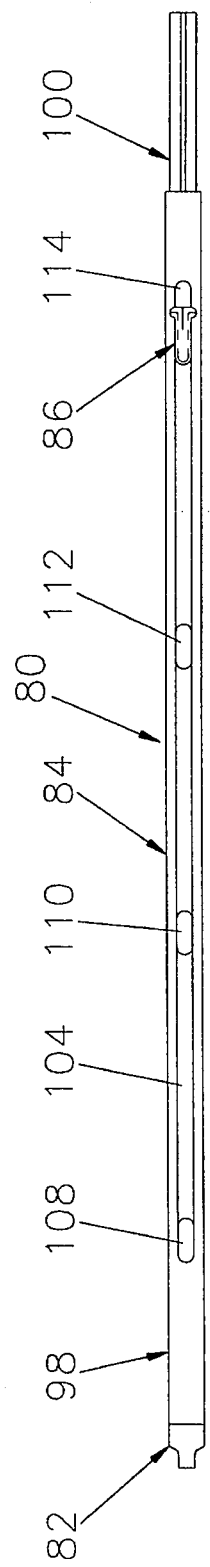
FIG. 8 is a side elevational view of an another embodiment of an anchor driver formed in accordance with the present invention.
Figure 9:
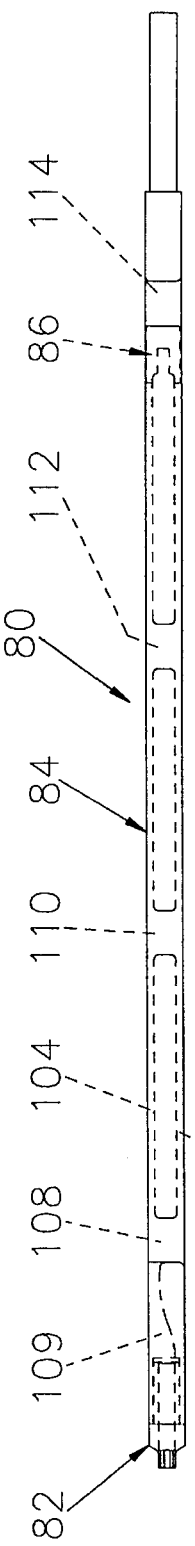
FIG. 9 is a side elevational view of the anchor driver shown in FIG. 8, rotated 90 degrees about its longitudinal axis, and showing the internal structure of the device in phantom.
Figure 10:
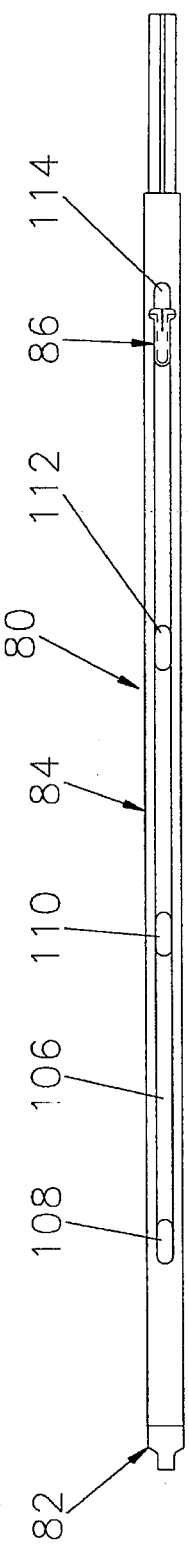
FIG. 10 is a side elevational view of the anchor driver shown in FIG. 8, rotated 180 degrees about its longitudinal axis.

In mounting the anchor 14, as described above, onto the driver 10 distal end, the suture 16, shown as two strands, ends are threaded through the anchor mount 13 coupling hole 20 and travel into and through a center longitudinal passage 21, shown best in FIG. 2, that is formed through an anchor mount stem end section 22 of the anchor mount 13. The stem end section 22 is of a diameter to fit tightly into an end center cavity 23 that is formed axially into the driver body 11 distal end, to mount the anchor mount 13 thereto. The anchor mount stem end section 22 center longitudinal passage 21 has a lesser diameter than does the coupling hole 20 disposed axially therewith from the anchor mount 13 distal end.

With the anchor mount 13 fitted into the driver body 11 distal end, as shown in FIG. 1, the center longitudinal passage 21 at its proximal end is aligned with a distal end 25 of a first curved passage 24 that is formed in the driver body. The curved passage 24, as shown, curves from its distal end 25 to an exit opening 26 in the driver body outer surface. Adjacent thereto, straight longitudinal groove 27 is formed in the surface of the driver body 11, from the first curved passage exit opening 26, across a midsection thereof, to a distal or inlet end 29 of a second curved passage 28, which second curved passage 28, extends through the driver body 11 to an exit opening 30. As shown, the exit end 26 of the first curved passage 24 and the exit end 30 of the second curved passage 28 are on opposite sides of the driver body 11. To load an anchor 14 suture 16 is threaded through the first curved passage 24, is maintained within the groove 27, and is fitted through the second curved passage 28 and is then held against the side of the driver body 11 so as to maintain the suture to the side of the driver body 11. Pulling which suture 16 through the driver body 11, as described pulls the anchor 14 tightly into the anchor mounting 13.

To provide for retaining the suture 16 on the side of the driver body 11 of the driver 10, as shown in FIGS. 1 through 5, a suture post 31 projects radially outwardly from driver 10. Suture post 31 terminates in an enlarged end cap 32. A resilient rubber grommet 35 is mounted on suture post 31 so as to be in compressed engagement between driver body 11 and end cap 32. During use, once suture 16 has been threaded through the driver's first curved passage 24 and second curved passage 28 so that it extends from exit opening 30, the suture is secured to suture post 31. More particularly, suture 16 is slid between rubber grommet 35 and either driver body 11 or the inner surface 36 (FIG. 5) of end cap 32. Suture 16 is then wrapped one or more times around suture post 31. As this is done, the resilient nature of rubber grommet 35 will provide an interference fit for suture 16 between the grommet and either driver body 11 or inner surface 36 of end cap 32.

With the suture 16 maintained to the side of driver body 11, as set out above, the driver can be fitted to be turned utilizing a T-handle inserter, or drill, not shown, whereby the anchor 14 mounted to the driver body 11 will be turned into a bone or bone like material. To facilitate which driver turning the driver body proximal end is provided with a triangular shaped straight sided section 33, that is shown in top view in FIG. 5, as a triangle with three equal sides. So arranged, the driver sided section 33 can be conveniently fitted into a chuck of a standard drill, onto the T-handle, or the like, not shown, for turning by operation thereof.

Preferably, driver 10 and anchor 14 are of the sort generally disclosed in U.S. Pat. No. 4,632,100, i.e., anchor 14 is designed to drill itself off the end of driver 10 when the anchor is drilled into bone. In such a case, it will be appreciated that suture 16 must be held to driver 10 in such a way that anchor 14 can separate from driver 10 at the appropriate moment. At the same time, however, it is also preferred that suture 16 be held relatively taught along the shaft of driver 10 prior to anchor deployment, whereby suture 16 can help keep the anchor in engagement with the distal end of the driver. These two respective interests can be accommodated with the apparatus shown in FIGS. 1–5 with two different arrangements.

In a first arrangement, the gripping engagement between suture 16 and resilient grommet 35 can be made loose enough such that the anchor can pull the suture off post 31 during anchor deployment, yet still firm enough that the suture provides some resistance to the anchor inadvertently falling off the distal end of the driver prior to deployment. Such an arrangement requires a careful balancing of the factors affecting suture retention, i.e., the size and elasticity of the rubber grommet, the size of the suture, coefficients of friction, the number of suture turns made around the post, etc.

In a second arrangement, the suture is made as fast as desired to post 31 at the time of assembly, but the suture end is loosened from post 31 by the manual intervention of the surgeon just prior to drilling the anchor into the bone. This arrangement provides some protection against the anchor inadvertently falling off the end of the driver prior to anchor deployment, yet still allows the anchor to separate from the driver at the appropriate moment.

FIGS. 6 and 7 show another embodiment of the invention, a suture anchor loader and driver 59, hereinafter referred to as driver 59. Driver 59 is like driver 10, except as to its arrangement for maintaining a suture 16 to a driver body 60. Driver body 60, it should be understood, includes the structure of the driver body 11, having a distal end 12, anchor mount 13, and first curved passage 24. Shown in FIG. 6, the driver body 60 also includes a slot 61, that is like groove 27, and intersects a second curved passage 62, that includes inlet and exit openings, 63 and 64, respectively. Which second curved passage has a rear wall 62a. The rear wall 62a, as shown, is adjacent to the edge of the exit opening 64, and is to receive the sutures 16 clamped thereagainst by operation of a spring biased clamp 65, as set out in detail hereinbelow.

Clamp 65 of driver 59 preferably has a profile of an alligator type clamp and includes a plate 66 that has a pair of parallel sections 67 extending at right angles downwardly from aligned mid points along opposite sides of the plate 66. The parallel sections 67 each include a hole formed therethrough, which holes are aligned and are to receive a pin 68 fitted therethrough. The pin 68 is fitted through the driver body 60 as a pivot mounting of the clamp 65 onto the driver body. A spring 69 is preferably positioned between the opposing surfaces of the driver body 60 and the undersurface of a broad end of plate 66. The spring 69 elevates the clamp 65 broad head end, as shown in solid lines in FIG. 6, such that a roughened or scored surface 72 that is formed across an undersurface at the end of a narrow forward portion of plate 66, is urged towards the rear wall 62a or the curved passage 62 to clamp the suture strands 16 thereagainst. So arranged, the suture 16 strands will be clamped against rear wall 62a by the clamp 65 scored end under surface 72 until released. Which release is provided, as shown in broken lines in FIG. 6, by an operator, shown as a thumb 70, depressing a roughened, scored, or like friction producing curved top surface 71 of the plate 66 broad or wide end to compress spring 69, and to thereby pivot the plate around pin 68, so as to elevate the plate rough end or scored surface 72 off of the suture 16 strands.

Referring now to FIGS. 8–18, a further embodiment of the invention comprises a suture anchor loader and driver 80, hereinafter referred to as driver 80. Driver 80 comprises a structure that is generally similar to the structure of the driver 10 shown in FIGS. 1–5, except as to its arrangement for maintaining a suture 16 to the driver. More particularly, driver 80 generally comprises an anchor mount 82, a cylindrical body 84, and a suture retaining plug 86 (FIGS. 8–11, 17 and 18).

Referring now to FIGS. 8–16, anchor mount 82 is substantially the same as anchor mount 13, having a cylindrical mid-section 88 (FIG. 16) that necks inwardly to a distal end 90. A central longitudinal anchor coupling hole 92 is longitudinally positioned within anchor mount 82, and is adapted to accept an anchor coupling end 15, as disclosed hereinabove. Coupling hole 92 communicates with a center longitudinal passage 94 that is formed through an anchor mount stem end section 96. Anchor mount 82 is assembled to cylindrical body 84 in the same manner as discussed above in connection with anchor mount 13 and driver body 11.

Cylindrical body 84 is generally similar to cylindrical body 11, except as to its arrangement for maintaining a suture 16 to the driver. More particularly, cylindrical body 84 comprises a distal end 98 (FIGS. 8 and 12) and a driver sided section 100 (FIGS. 8, 12 and 13) that is disposed in spaced relation to distal end 98. Distal end 98 is adapted to accept stem end section 96 of anchor mount 82 (FIG. 16) in the same manner as disclosed above in connection with driver body 11 and anchor mount 13. Similarly, driver sided section 100 (FIGS. 8 and 12) is adapted to be installed in a T-handle or drill as disclosed hereinabove.

Cylindrical body 84 differs from body 11 in its arrangement for maintaining a suture 16 to the driver. More particularly, cylindrical body 84 comprises two longitudinal grooves 104 and 106 (FIGS. 8–12 and 14–16), and four transverse passageways 108 (FIGS. 8–12 and 14–16), 110 (FIGS. 8–11), 112 (FIGS. 8–11), and 114 (FIGS. 8–12 and 14–16). Longitudinal grooves 104 and 106 are disposed in substantially parallel relation to one another, on diametrically-opposing sides of cylindrical body 84. Grooves 104 and 106 are adapted to receive suture 16, as will hereinafter be disclosed in further detail.

Figure 11:
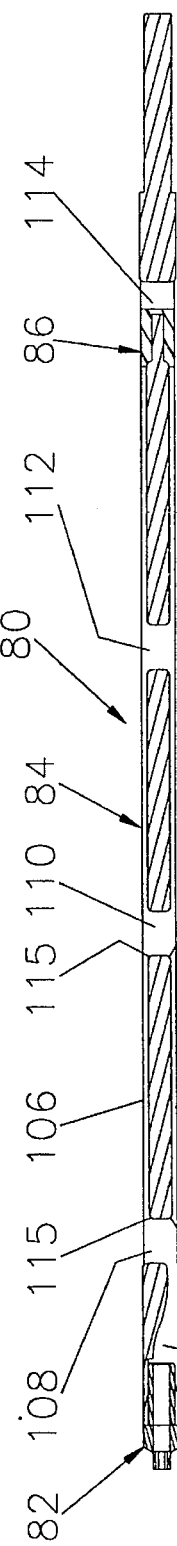
FIG. 11 is a cross-sectional view of the anchor driver shown in FIG. 8, rotated 270 degrees about its longitudinal axis.
Figure 12:
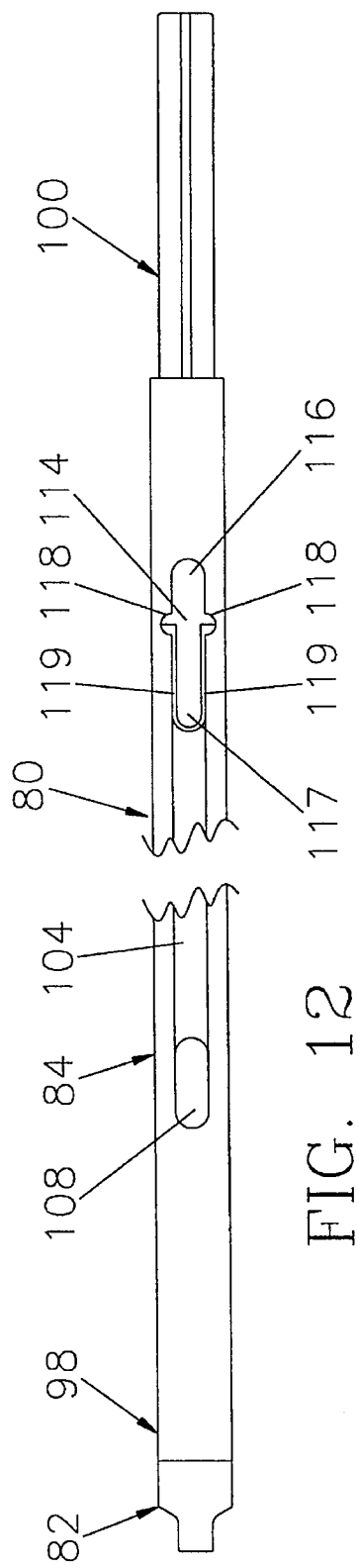
FIG. 12 is an enlarged side elevational view of the anchor driver shown in FIG. 8, with the driver's suture retaining plug having been removed from the drawing.
Figure 13:
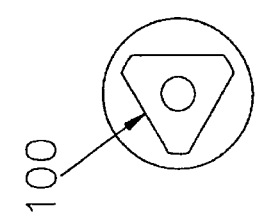
FIG. 13 is an end view of the driver shown in FIG. 12.
Figure 14:
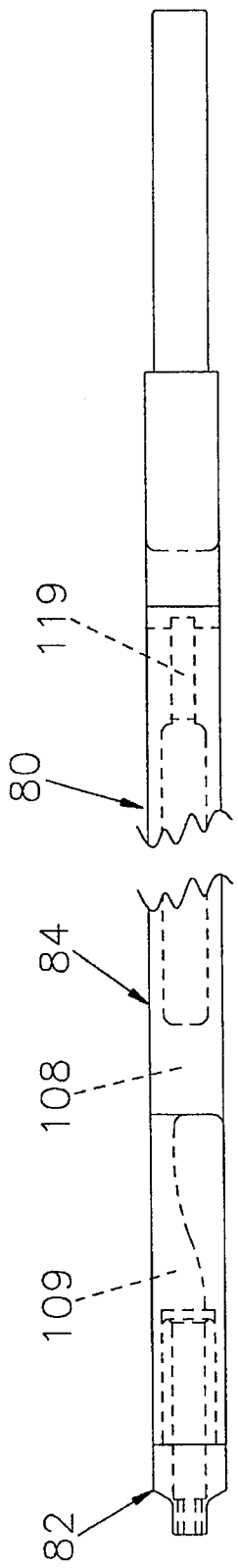
FIG. 14 is an enlarged side elevational view of the anchor driver shown in FIG. 9, with the driver's suture retaining plug having been removed from the drawing.
Figure 26:
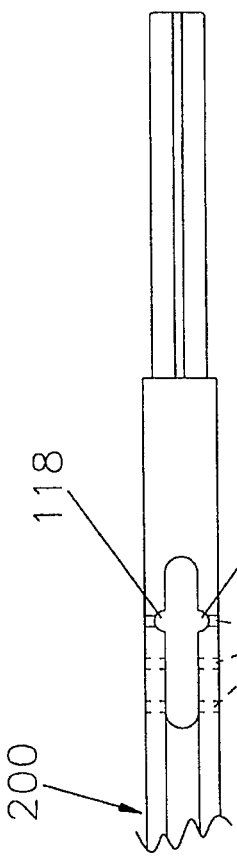
FIG. 26 is an enlarged side elevational view of the anchor driver shown in FIG. 21, with the driver's suture retaining plug having been removed from the drawing.
Figure 27:
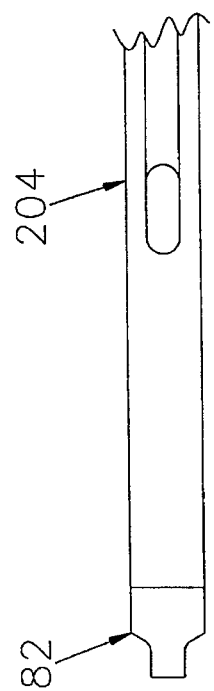
FIG. 27 is an enlarged cross-sectional view of the driver shown in FIG. 22, with the driver's suture retaining plug having been removed from the drawing.

Passageways 108, 110, 112 and 114 are disposed along, and extend radially through, cylindrical body 84 so as to communicate between longitudinal grooves 104 and 106 (FIG. 11). Each passageway 108, 110, 112 and 114 defines a generally oval-shaped hole at the point where it communicates with grooves 104 and 106. Each passageway 108, 110, 112 and 114 includes rounded edges 115 (FIG. 11) at its intersection with grooves 104 and 106 so as to prevent fraying or cutting of suture 16 when the suture passes therethrough.

Passageway 108 communicates with a curved passageway 109 (FIGS. 9, 11, 14, and 16) that is substantially the same as first curved passageway 24 of cylindrical body 11. Curved passageway 109 communicates between passage 94 of anchor mount 82 and passageway 108 of cylindrical body 84. Curved passageway 109 also communicates with longitudinal groove 104.

Passageways 110 and 112 (FIGS. 8–11) are disposed in equidistant relation along cylindrical body 84, between passageways 108 and 114.

Referring now to FIGS. 12 and 14–16, passageway 114 is disposed adjacent to driver sided section 100. Passageway 114 differs from passageways 108, 110 and 112 in that it comprises an upper section 116 (FIG. 12), a lower section 117, four rounded cut-outs 118 (FIGS. 12 and 15) and a side stabilizer 119 (FIGS. 12 and 14–16). More particularly, rounded cut-outs 118 are disposed in opposing relation to one another on either side of longitudinal groove 104 (FIG. 12) and on either side of longitudinal groove 106, between upper section 116 and lower section 117 of passageway 114. Cut-outs 118 are adapted to prevent suture retaining plug 86 from travelling longitudinally within passageway 114, as will hereinafter be disclosed in further detail.

Side stabilizer 119 (FIGS. 12 and 14–16) comprises a rib that projects inwardly into passageway 114 from three sides of lower section 117. Side stabilizer 119 extends into passageway 114 so as to engage a portion of suture retaining plug 86, as will hereinafter be disclosed in further detail.

Referring now to FIGS. 17 and 18, suture retaining plug 86 comprises a resilient elastomeric body having a side stabilizing groove 124, four locking tabs 126, and a slit 128.

More particularly, suture retaining plug 86 includes a top portion 130, a rounded bottom portion 132, side portions 133 and 134, and face portions 135 and 136. Suture retaining plug 86 is sized and shaped so as to fit completely within passageway 114 so that face portions 135 and 136 do not extend beyond the floor of longitudinal grooves 104 and 106.

Side stabilizing groove 124 runs along suture retaining plug 86, from the top of side portion 133, across rounded bottom portion 132, and back up to the top of side portion 134. Groove 124 is preferrably positioned mid-way between face portions 135 and 136 (FIG. 17). Groove 124 is sized and shaped so as to accept the driver's side stabilizer 119 when plug 86 is positioned within the driver's passageway 114, as will hereinafter be disclosed in further detail.

The plug's four locking tabs 126 project laterally from top portion 130, with one tab being disposed on each side of groove 124, adjacent to face portions 135 and 136. Locking tabs 126 are sized and shaped so as to tightly fit within the driver's cut-outs 118 when suture retaining plug 86 is positioned within passageway 114, as will hereinafter be disclosed in further detail.

Slit 128 extends downwardly into plug 86 from top portion 130. Slit 128 extends between face portions 135 and 136. Slit 128 is arranged so that it will be aligned with grooves 104 and 106, and with passageway 114, when suture retaining plug 86 is positioned within passageway 114. Slit 128 is normally pressed closed by the walls of passageway 114 so as to (i) hold suture 16 in place during turning of driver 80, and (ii) allow suture 16 to slidingly release from plug 86 when necessary, as will hereinafter be disclosed in further detail.

Driver 80 is assembled in a manner similar to that of driver 10 disclosed hereinabove, except with regard to suture retaining plug 86 and suture 16.

More particularly, suture retaining plug 86 is assembled to cylindrical body 84 by first orienting plug 86 so that its rounded bottom portion 132 is positioned just above lower section 117 of passageway 114. From this position, suture retaining plug 86 is moved into passageway 114. Once the plug's bottom portion 132 has entered the driver's passageway 114, suture retaining plug 86 is moved distally with respect to cylindrical body 84. As this occurs, the driver's side stabilizer 119 slidingly enters the plug's groove 124. Suture retaining plug 86 is moved distally within passageway 114 until the plug's bottom portion 132 engages the distalmost portion of lower section 117 of passageway 114. When the plug's bottom portion 132 engages the distalmost portion of lower section 117 of passageway 114, the driver's side stabilizer 119 will be fully received within the plug's groove 124. At the same time, the plug's four locking tabs 126 each snap into the driver's four cut-outs 118 so as to (i) compressively fix suture retaining plug 86 within passageway 114, and (ii) press slit 128 closed. When suture retaining plug 86 has been positioned in passageway 114 in the foregoing manner, the passageway's upper section 116 will remain open so as to receive a suture therethrough, as will hereinafter be discussed in further detail.

It should be understood that the interaction of the plug's locking tabs 126 with the driver's cut-outs 118 prevents longitudinal movement of suture retaining plug 86 within passageway 114. It should also be understood that the interaction of the driver's side stabilizer 119 and the plug's groove 124 prevents relative side movement of suture retaining plug 86 within passageway 114. As a result of the foregoing construction, suture retaining plug 86 is securely maintained within passageway 114, with the plug's face portions 135 and 136 not extending beyond the floor of driver grooves 104 and 106.

With anchor mount 82 in place in distal end 98 of cylindrical body 84, and suture retaining plug 86 in place in passageway 114, anchor 14 and suture 16 can be assembled to driver 80. More particularly, suture 16 is first threaded through coupling end 15 of anchor 14 so as to firmly engage anchor 14, as disclosed hereinabove. The free ends of suture 16 are then threaded through coupling hole 92, center longitudinal passage 94, passageway 109 and passageway 108. In this position, suture 16 extends outwardly from passageway 108 and groove 106. Suture 16 is then threaded up along longitudinal groove 104 and then through the upper section 116 of passageway 114 so that the free end of the suture exits on the opposite side of the driver.

Once in this position, suture 16 may be slidingly secured to suture retaining plug 86. More particularly, the free ends of suture 16 are first drawn outwardly and upwardly so as to take up any slack along the length of suture 16. This movement also tends to draw suture 16 into groove 104, where it will be protected during operation of driver 80. This procedure also has the effect of pulling coupling end 15 of anchor 14 into firm engagement with anchor coupling hole 92. The free ends of suture 16 are then pulled downwardly so that suture 16 is pulled down into slit 128. As this occurs, plug 86 separates at slit 128 so as to grippingly accept suture 16. Once suture 16 has been so secured to suture retaining plug 86, the free ends of suture 16 may be brought back along groove 106 and passed back through one of the passageways 108, 110 or 112. In this way the free ends of suture 16 may be releasably attached to driver 80.

As a result of this arrangement, suture 16 is held firmly within suture retaining plug 86, via slit 128, so as to help hold anchor 14 to driver 80 prior to installation of the anchor in a target bone. At the same time however, suture 16 is able to slidingly disengage from plug slit 128 when anchor 14 drills itself off the driver as the anchor is deployed in the target bone.

Referring now to FIGS. 19–29, a further embodiment of the invention comprises a suture anchor loader and driver 200, hereinafter referred to as driver 200. Driver 200 comprises a structure which is generally similar to the structure of the driver 80 shown in FIGS. 8–18, except as to its arrangement for mounting the suture retaining plug to the driver shaft. More particularly, with the driver 80 shown in FIGS. 8–18, driver 80 and suture retaining plug 86 are formed separately from one another, and then the two members are mechanically assembled to one another so as to together form a complete driver assembly. Contrastingly, with the driver 200 shown in FIGS. 19–29, the suture retaining plug 202 (FIGS. 19–22, 28 and 29) is intended to be insert molded directly onto the driver's shaft so as to thereby form the complete driver assembly.

To this end, driver 200 comprises an anchor mount 82 and a cylindrical body 204 (FIGS. 19–23 and 25–27). Anchor mount 82 of driver 200 is identical to the anchor mount 82 of driver 80, i.e., it comprises a cylindrical mid-section 88 (FIG. 27), a distal end 90, a central longitudinal anchor coupling hole 92, a center longitudinal passage 94, and an anchor mount stem end section 96. Similarly, cylindrical body 204 is very similar to the cylindrical body 84, i.e., it comprises a distal end 98 (FIG. 19), a driver sided section 100, two longitudinal grooves 104 and 106 (FIGS. 19 and 21), four transverse passageways 108, 110, 112 and 114 (FIG. 22) each having rounded edges 115, and a curved passageway 109.

Cylindrical body 204 of driver 200 differs from cylindrical body 82 of driver 80 in that the side stabilizer 119 of driver 80 is replaced with a plurality of side openings 206 in driver 200 (FIGS. 23 and 25–27). Each of the side openings 206 extends through the side wall of the driver in the manner shown in FIGS. 23 and 25–27.

Figure 28:
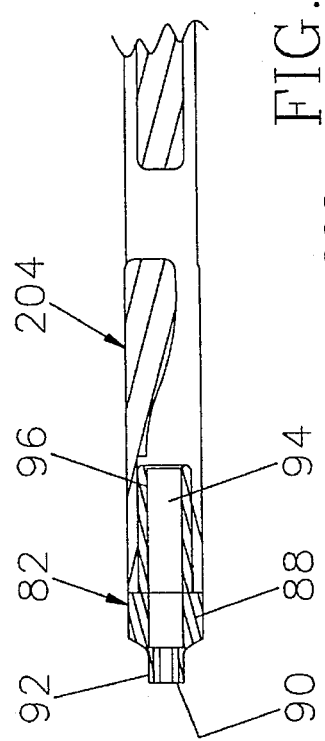
FIG. 28 is an enlarged side elevational view of the suture retaining plug employed in the driver of FIGS. 19–22.
Figure 29:
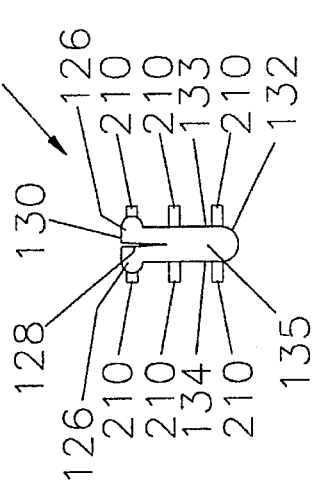
FIG. 29 is an enlarged side elevational view of that same suture retaining plug, with the suture retaining plug having been rotated 90 degrees from the position shown in FIG. 28.

Driver 200 also comprises a suture retaining plug 202 (FIGS. 19–22, 28 and 29). Suture retaining plug 202 is insert molded out of a suitable elastomeric or polymeric material directly onto the driver's cylindrical body 204 in ways well known in the art. Suture retaining plug 202 of driver 200 is identical to the suture retaining plug 86 of driver 80, except as will hereinafter be disclosed in further detail. More particularly, suture retaining plug 202 comprises a top portion 130 (FIG. 29), a rounded bottom portion 132, side portions 133 and 134, and face portions 135 and 136 (FIGS. 28 and 29). Suture retaining plug 202 also comprises four locking tabs 126 and a slit 128.

However, suture retaining plug 202 omits the side stabilizing groove 124 which is provided in the aforementioned suture retaining plug 86. Instead, suture retaining plug 202 includes a plurality of side projections 210 which project laterally outward from side portions 133 and 134. Side projections 210 are formed when the melt material flows into the shaft's side openings 206 during insert molding. Side projections 210 help stabilize suture retaining plug 202 relative to the driver's shaft, just as the suture retaining plug's four locking tabs 126 engage the driver's cut-outs 118 (FIGS. 23 and 26) so as to stabilize the plug relative to the shaft.

Driver 200 is intended to be used in the same manner as driver 80.

Figure 30:
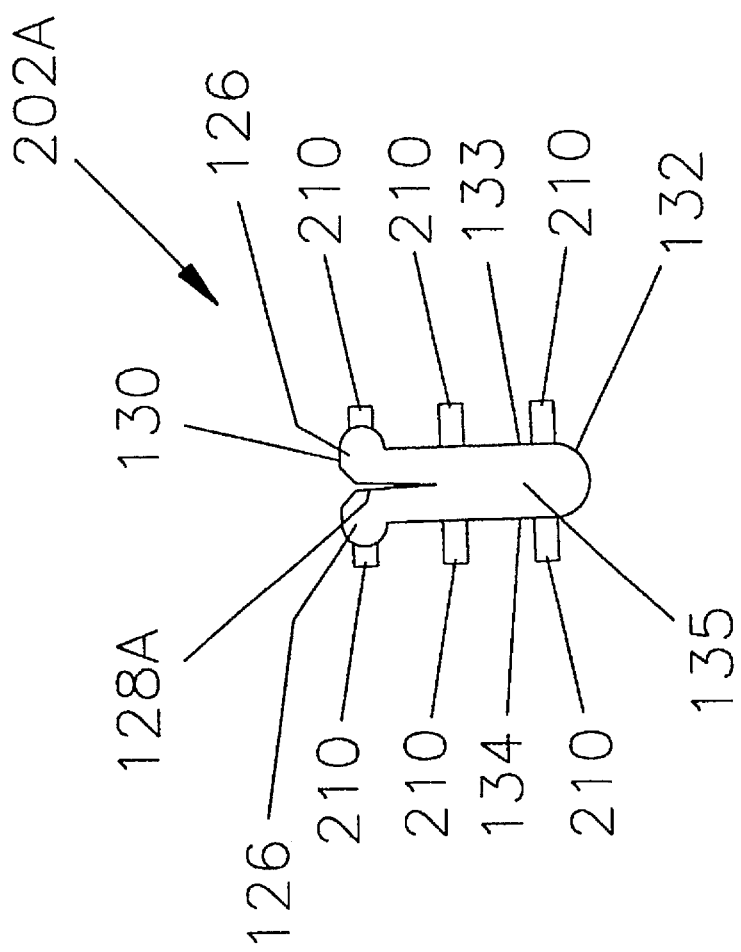
FIG. 30 is an enlarged side elevational view of an alternative embodiment of the suture retaining plug, showing a chamfered lead-in formed at the entrance to the slit.

It is also possible to provide a chamfered lead-in for the plug's slit 128 to facilitate entry of suture 16 into the slit. See, for example, the slit 128A provided in the plug 202A shown in FIG. 30.

It is also possible to modify driver 200 by omitting suture retaining plug 202 and by omitting the shaft's side openings 206. In this case, passageway 114 would remain completely open, in a manner similar to passageways 108, 110 and 112. In use, suture 16 would be threaded through coupling hole 92, through center longitudinal passageway 94, through passageway 109, through passageway 108, along longitudinal groove 104, through passageway 114, back down groove 106 and then through one of the passageways 108, 110 or 112. With such an arrangement, suture 16 will tend to be held fairly loosely to the driver's shaft; however, in many situations such a suture attachment will be adequate.

It is also possible to modify driver 200 (or driver 10 or driver 59 or driver 80) so that the anchor mount and the shaft are formed out of a single member, or to modify driver 200 (or driver 10 or driver 59 or driver 80) so that the anchor mount is molded onto the shaft or the shaft is molded onto the anchor mount.

It is also to be appreciated that, while in the foregoing description drill-type anchors have been discussed, it is also possible to practice the present invention with alternative types of anchors and their associated installation tools. By way of example, it is possible to practice the present invention with barb-type anchors of the sort set with a plunging motion, e.g. anchors of the sort taught in U.S. Pat. Nos. 4,898,156; 4,968,315; 5,207,679; and 5,217,486, which patents are hereby incorporated herein by reference. In such a case, the distal end of the driver would be modified as appropriate to mate with the barb-type anchor, and the anchor would be deployed with a distally-directed driving motion of the driver.

While preferred embodiments of our invention in a suture anchor loader and driver have been shown and described herein, it should be understood that the present disclosure is made by way of example only and that variations to the invention and its use are possible within the scope of this disclosure without departing from the subject matter coming within the scope of the following claims, and a reasonable equivalency thereof, which claims we regard as our invention.

We claim:

1. A suture anchor loader and driver comprising a driver body including a cylindrical portion, an anchor mount disposed at a distal end of said cylindrical portion, a proximal end of said cylindrical portion having extending therefrom a flat-sided section for mounting said cylindrical portion to a chuck portion of a means for driving said driver body, said anchor mount having a center longitudinal opening formed therethrough and including an anchor coupling means formed in a distal end of said anchor mount that is to receive a coupling end of an anchor device fitted axially therein, said driver body having at least a first internal passage therein intersecting and extending from said anchor mount longitudinal opening, and exiting on a driver body side surface proximate but spaced from said cylindrical portion distal end, and means associated with said cylindrical portion, for retaining a suture that is secured to said anchor device and extending through said anchor mount longitudinal opening, and extending through said first passage, and along said driver body.

2. A suture anchor loader and driver as recited in claim 1, further including a straight longitudinal groove formed in said driver body side surface and extending from an exit end of the first passage.

3. A suture anchor loader and driver as recited in claim 1 wherein said means for retaining a suture alongside said driver comprises a post extending laterally outward from said driver body, a cap extending transversely to said post, and an elastomeric body disposed on said post between said cap and said driver body.

4. A suture anchor loader and driver comprising a driver body including a cylindrical portion, an anchor mount disposed at a distal end of said cylindrical portion, a proximal end of said cylindrical portion including means for mounting said cylindrical portion to a means for driving said driver body, said anchor mount having a center longitudinal opening formed therethrough and including an anchor coupling means formed in a distal end of said anchor mount that is to receive a coupling end of an anchor device fitted axially therein, said driver body having at least a first passage formed from a driver body distal end, intersecting said anchor mount longitudinal opening, and exiting a driver body surface, and means for retaining a suture that is secured to said anchor device and extending through said anchor mount longitudinal opening, and extending through said first passage, and along said driver body, a straight longitudinal groove formed in the driver body surface and extending from an exit end of the first passage, and a second passage formed through the driver body whose entrance is at a proximal end of the longitudinal groove, and is formed through said driver body exiting on a second side of said driver body opposite to the first passage exit end and said longitudinal groove.

5. A suture anchor loader and driver as recited in claim 4, wherein the means for retaining a suture along said driver body is a clamp means that includes a flat plate that has a broad rear end and narrow forward end and, at a mid-section, is pivotally mounted onto the second side of said driver body, whereby, when said plate is pivoted to where an end of said plate narrow forward end engages said driver body, a lower edge portion of said plate narrow forward end extends into an exit end of the second passage to engage an adjacent wall of said second passage, and means for biasing said plate broad rear end away from said driver body such that said plate narrow end lower edge portion will engage said second passage adjacent wall.

6. A suture anchor loader and driver as recited in claim 5, wherein the means for biasing said plate broad rear end is a spring that is maintained between an undersurface of said plate broad rear end and the surface of the driver body, which said spring biasing is overcome by depressing a top surface of said plate broad rear end, and the lower edge portion of said plate narrow forward end includes a roughened surface for engaging the suture.

7. A suture anchor loader and driver comprising a driver body including a cylindrical portion, an anchor mount disposed at a distal end of said cylindrical portion, a proximal end of said cylindrical portion including means for mounting said cylindrical portion to a means for driving said driver body, said anchor mount having a center longitudinal opening formed therethrough and including an anchor coupling means formed in a distal end of said anchor mount that is to receive a coupling end of an anchor device fitted axially therein, said driver body having at least a first passage formed from a driver body distal end, intersecting said anchor mount longitudinal opening, and exiting a driver body surface, and means for retaining a suture that is secured to said anchor device and extending through said anchor mount longitudinal opening, and extending through said first passage, and along said driver body, and two straight longitudinal grooves formed in the driver body surface on diametrically opposing sides thereof, each of said grooves extending from an exit end of said first passage to a second passage formed through said driver body.

8. A suture anchor loader and driver as recited in claim 7, wherein said means for retaining said suture along said driver comprises a resilient plug lodged within a portion of said second passage, said plug comprising separable gripping means for (i) holding said suture during driving of said driver, and (ii) allowing said suture to slidingly disengage from said plug as said anchor device is deployed in a target bone.

9. A suture anchor loader and driver as recited in claim 8, comprising at least one additional passage communicating between said two longitudinal grooves and positioned between said first and second passages.

10. A suture anchor loader and driver as recited in claim 9 comprising means for retaining the suture within at least one of said grooves while said suture is gripped by said separable gripping means.

11. A suture anchor loader and driver as recited in claim 10 comprising means for retaining the suture within the other of said grooves, and further wherein said suture is extendable through said at least one additional passage.

12. A suture anchor loader and driver as recited in claim 8, wherein said separable gripping means comprise a slit extending downwardly into a portion of said plug, said slit being in communicating alignment with said two longitudinal grooves and said second passage so as to be capable of grippingly accepting said suture.

13. A suture anchor loader and driver as recited in claim 12, wherein said second passage includes at least two cut-outs positioned in opposing relation to one another within walls of said second passage, said cut-outs being adapted to accept corresponding locking tabs disposed on an outer surface of said plug so as to prevent longitudinal movement of said plug within said second passage.

14. A suture anchor loader and driver as recited in claim 13, wherein said second passage includes a rib that projects inwardly into a portion of said second passage so as to engage a corresponding grooved portion of said plug and thereby prevent transverse movement of said plug within said second passage.

15. A suture anchor loader and driver as recited in claim 8, wherein said driver body includes a plurality of openings extending between said second passage and said driver body surface, and said plug comprises a plurality of lateral projections for seating in said openings.

16. A method of deploying an anchor device in bone comprising the steps of:

(1) providing a suture anchor loader and driver comprising a driver body including a cylindrical portion, an anchor mount disposed at a distal end of said cylindrical portion, a proximal end of said cylindrical portion having extending therefrom a flat-sided section for mounting said cylindrical portion to a chuck portion of a means for driving said driver body, said anchor mount having a center longitudinal opening formed therethrough and including an anchor coupling means formed in a distal end of said anchor mount that is to receive a coupling end of an anchor device fitted axially therein, said driver body having at least a first internal passage intersecting and extending from said anchor mount longitudinal opening, and exiting on a driver body side surface proximate but spaced from said cylindrical portion distal end, and means for retaining a suture that is secured to said anchor device and extending through said anchor mount longitudinal opening, and extending through said first passage, and along said driver body;

(2) threading said suture through said coupling end of said anchor device;

(3) threading said suture through said anchor mount longitudinal opening and said first passage;

(4) engaging said suture with said means for retaining said suture such that said suture is retained along said driver body; and (5) driving said driver so as to deploy said anchor device in the bone.

* * * * *